United States Patent

Duckworth et al.

[11] Patent Number: 5,834,471
[45] Date of Patent: Nov. 10, 1998

[54] AMIDE DERIVATIVES AS $5HT_{1D}$ RECEPTOR ANTAGONISTS

[75] Inventors: David Malcolm Duckworth, Hertfordshire; Sarah Margaret Jenkins, Essex; Andrew John Jennings, Hertfordshire, all of England

[73] Assignee: SmithKline Beecham p.l.c., Brentford, England

[21] Appl. No.: 591,553

[22] PCT Filed: Jul. 26, 1994

[86] PCT No.: PCT/EP94/02492

§ 371 Date: Feb. 2, 1996

§ 102(e) Date: Feb. 2, 1996

[87] PCT Pub. No.: WO95/04729

PCT Pub. Date: Feb. 16, 1995

[30] Foreign Application Priority Data

Aug. 6, 1993 [GB] United Kingdom .................. 9316328
Aug. 9, 1993 [GB] United Kingdom .................. 9316496

[51] Int. Cl.⁶ ...................... A61K 31/495; C07D 407/14; C07D 409/14; C07D 295/155
[52] U.S. Cl. .................. 514/252; 514/235.8; 514/255; 544/121; 544/357; 544/364; 544/366; 544/370; 544/371; 544/365; 544/379; 544/393

[58] Field of Search ...................... 544/121, 357, 544/364, 366, 370, 371, 379, 393, 365; 514/235.8, 252, 255

[56] References Cited

U.S. PATENT DOCUMENTS 5,340,810 8/1994 Clitherow et al. ...................... 544/393
5,356,893 10/1994 Bradshaw et al. ...................... 544/393

FOREIGN PATENT DOCUMENTS 0 533 266 A1 3/1993 European Pat. Off. .
0 533 267 A1 3/1993 European Pat. Off. .
0 533 268 A1 3/1993 European Pat. Off. .

OTHER PUBLICATIONS

John W. Clitherow, et al., "Evolution of a Novel Series of [(N,N–Dimethylamin)propl]–and Piperazinylbenzanilides as the First Selective 5–HT1D Antagonists", *Journal of Medicinal Chemistry*, vol. 37, No. 15, pp. 2253–2257 (Jul. 22, 1994).

Saxena et al.. *Pharmac. Ther.*vol.66,p.339–368, 1995.

*Primary Examiner*—Emily Bernhardt
*Attorney, Agent, or Firm*—Wayne J. Dustman; Charles M. Kinzig; Stephen Venetianer

[57] ABSTRACT

Novel amide derivatives, processes for their preparation, and pharmaceutical compositions containing them are disclosed.

8 Claims, No Drawings

AMIDE DERIVATIVES AS 5HT$_{1D}$ RECEPTOR ANTAGONISTS

The present invention relates to novel amide derivatives, processes for their preparation, and pharmaceutical compositions containing them.

EPA 0 533 266/7/8 disclose a series of benzanilide derivatives which are said to possess 5HT$_{1D}$ receptor antagonist activity. These compounds are alleged to be of use in the treatment of various CNS disorders.

A structurally distinct class of compounds have now been discovered and have been found to exhibit 5HT$_{1D}$ antagonist activity. In a first aspect, the present invention therefore provides a compound of formula (I) or a salt thereof:

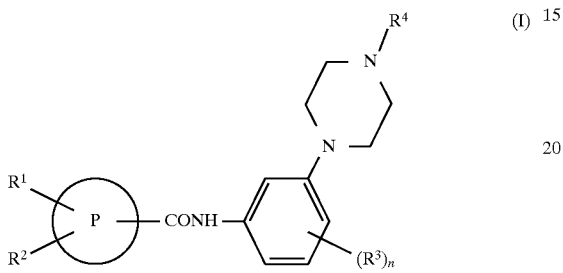

in which
P is a phenyl or a 5 or 6-membered heterocyclic ring containing 1 or 2 heteroatoms selected from oxygen, nitrogen or sulphur,
R$^1$ is halogen, C$_{1-6}$alkyl, C$_{1-6}$cycloalkyl, optionally substituted phenyl or an optionally substituted 5–7-membered heterocyclic ring containing 1 to 3 heteroatoms selected from oxygen, nitrogen or sulphur,
R$^2$ is hydrogen, halogen, C$_{1-6}$alkyl, C$_{1-6}$alkoxy, nitro, trifluoromethyl or cyano;
R$^3$ is hydrogen, halogen, hydroxy, C$_{1-6}$alkyl or C$_{1-6}$alkoxy;
R$^4$ is hydrogen or C$_{1-6}$alkyl; and
n is 1 or 2,
provided that when P is phenyl R$^1$ is not pyridyl or phenyl.

C$_{1-6}$alkyl groups, whether alone or as part of another group, may be straight chain or branched.

Suitably P is a phenyl or a 5 or 6-membered heterocyclic ring containing 1 or 2 heteroatoms selected from oxygen, nitrogen or sulphur. Examples of rings P include pyridyl, thienyl, furyl and pyrrolyl rings. Preferably P is phenyl, thienyl, furyl or pyridyl.

Suitably R$^1$ is halogen, C$_{1-6}$alkyl, C$_{1-6}$cycloalkyl, optionally substituted phenyl or an optionally substituted 5–7-membered heterocyclic ring containing 1 to 3 heteroatoms selected from oxygen, nitrogen or sulphur. The group R$^1$ can be an aromatic or saturated heterocyclic ring. When R$^1$ is an aromatic heterocyclic ring, examples of such rings include pyridyl, thienyl, furyl, pyrrolyl, oxadiazolyl, pyrazolyl, triazolyl, diazolyl, isothiazolyl, isoxazolyl, thiadiazolyl, pyrimidyl and pyrazinyl. When R$^1$ is a saturated ring examples include piperidine, morpholine and piperazine rings. Optional substituents for R$^1$ include halogen, C$_{1-6}$alkyl, C$_{1-6}$alkoxy, hydroxy, cyano, nitro, amino, CO$_2$R$^5$ where R$^5$ is hydrogen or C$_{1-6}$alkyl or CONR$^6$R$^7$ where R$^6$ and R$^7$ are independently hydrogen or C$_{1-6}$alkyl.

Preferably R$^1$ is halogen, butyl, cyclohexyl, pyridyl, pyrazolyl, triazolyl, imidazolyl, morpholinyl, piperazinyl or thienyl.

Suitably R$^2$ is hydrogen, halogen, C$_{1-6}$alkyl, C$_{1-6}$alkoxy or nitro. Preferably R$^2$ is hydrogen, C$_{1-6}$alkoxy, for example methoxy, C$_{1-6}$alkyl, for example methyl, or nitro.

Suitably R$^3$ is hydrogen, halogen, hydroxy, C$_{1-6}$alkyl or C$_{1-6}$alkoxy. Preferably R$^3$ is C$_{1-6}$alkoxy such as methoxy.

Preferably n is 1 and the group R$^3$ is para to the amide linkage.

Suitably R$^4$ is hydrogen or C$_{1-6}$alkyl. Preferably R$^4$ is C$_{1-6}$alkyl such as methyl.

Particularly preferred compounds include:
N-[4-methoxy-3-(4-methyl-1-piperazinyl)phenyl]-5-(4-pyridyl)furan-2-carboxamide,
N-[4-methoxy-3-(4-methyl-1-piperazinyl)phenyl]-5-(4-pyridyl)furan-3-carboxamide,
N-[4-methoxy-3-(4-methyl-1-piperazinyl)phenyl]-5-(4-pyridyl)thiophene-2-carboxamide,
N-[4-methoxy-3-(4-methyl-1-piperazinyl)phenyl]-2-(4-pyridyl)pyridine-5-carboxamide,
N-[4-methoxy-3-(4-methyl-1-piperazinyl)phenyl]-2-(4-pyridyl)-3-methoxythiophene-4-carboxamide,
N-[4-methoxy-3-(4-methyl-1-piperazinyl)phenyl]-5-(2-pyridyl)thiophene-2-carboxamide,
N-(4-Methoxy-3-(4-methyl-1-piperazinyl)phenyl)-4-(1,2,4-triazol-1-yl) benzamide,
N-(4-Methoxy-3-(4-methyl-1-piperazinyl)phenyl)-4-(imidazol-1-yl) benzamide,
N-(4-Methoxy-3-(4-methyl-1-piperazinyl)phenyl)-4-(morpholin-1-yl) benzamide,
N-(4-Methoxy-3-(4-methyl-1-piperazinyl)phenyl)-4-(3-thiophenyl)-3-methylbenzamide,
N-(4-methoxy-3-(4-methyl-1-piperazinyl)phenyl)-4-(1,2,4-triazol-1-yl)-3-nitrobenzamide,
N-(4-Methoxy-3-(4-methyl-1-piperazinyl)phenyl)-3-nitro-4-pyrazolylbenzamide,
N-(4-Methoxy-3-(4-methyl-1-piperazinyl)phenyl)-4-(4-ethoxycarbonylpiperazin-1-yl)benzamide,
N-(4-Methoxy-3-(4-methyl-1-piperazinyl)phenyl)-4-fluorobenzamide,
N-(4-Methoxy-3-(4-methyl-1-piperazinyl)phenyl)-4-chlorobenzamide,
N-(4-Methoxy-3-(4-methyl-1-piperazinyl)phenyl)-4-iodobenzamide,
N-(4-Methoxy-3-(4-methyl-1-piperazinyl)phenyl)-4-cyclohexylbenzamide,
N-(4-Methoxy-3-(4-methyl-1-piperazinyl)phenyl)-4-tert-butylbenzamide, or a pharmaceutically acceptable salt thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in steroisomeric forms. It will be understood that the invention encompasses all geometric and optical isomers of the compounds of formula (I) and the mixtures thereof including racemates. Tautomers of compounds of formula (I) and mixtures thereof also form an aspect of the invention.

In a further aspect the present invention provides a process for the preparation of a compound of formula (I) which comprises.

(a) reaction of a compound of formula (II):

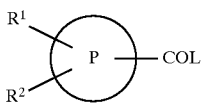
(II)

in which $R^1$, $R^2$ and P are as defined in formula (I) and L is a leaving group, with a compound of formula (III):

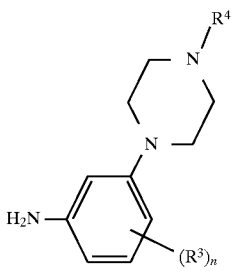
(III)

in which $R^3$, $R^4$ and n are as defined in formula (I);

(b) for compounds of formula (I) in which $R^1$ is a phenyl or heterocyclic ring reaction of a compound of formula (IV):

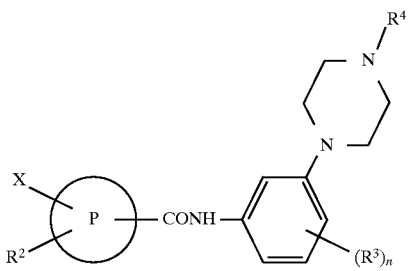
(IV)

in which $R^2$, $R^3$, $R^4$, P and n are as defined in formula (I) and X is a leaving group with a nucleophile $R^1$ where $R^1$ is as defined in formula (I); or (c) reaction of a compound of formula (V):

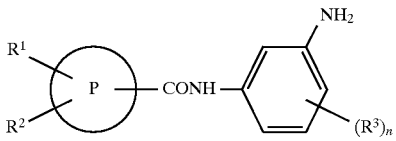
(V)

in which $R^1$, $R^2$, $R^3$, P and n are as defined in formula (I) with a compound of formula (VI):

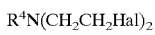
$R^4N(CH_2CH_2Hal)_2$ (VI)

in which $R^4$ is as defined in formula (I) and Hal is halogen, or (d) reaction of a compound of formula (VII):

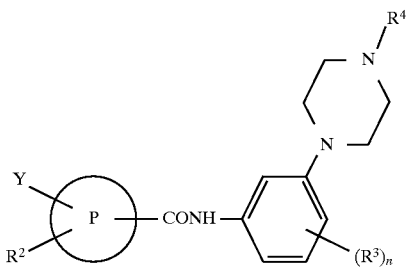
(VII)

in which $R^2$, $R^3$, $R^4$, P and n are as defined in formula (I) and Y is halogen or a group —$OSO_2CF_3$ with a compound of formula (VIII):

$R^1B(OH)_2$ (VIII)

in which $R^1$ is as defined in formula (I), or (e) reaction of a compound of formula (IX):

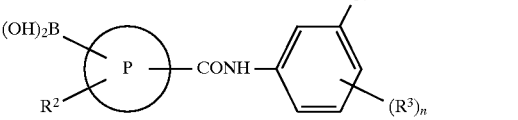
(IX)

in which $R^2$, $R^3$, $R^4$, P and n are as defined in formula (I) with a compound of formula (X):

$R^1Y$ (X)

in which $R^1$ is as defined in formula (I) and Y is as defined in formula (VII), and optionally thereafter:

converting a compound of formula (I) into another compound of formula (I)

forming a pharmaceutically acceptable salt.

Suitable activated carboxylic acid derivatives of formula (II) include acyl halides and acid anhydrides. Activated compounds of formula (II) can also be prepared by reaction of the corresponding carboxylic acid with a coupling reagent such as carbonyldiimidazole, dicyclohexylcarbodiimide or diphenylphosphorylazole. Preferably the group L is halo, particularly chloro.

A compound of formula (II) is typically reacted with a compound of formula (III) in an inert organic solvent such as DMF, ThF or dichloromethane at ambient or elevated temperature in the presence of a base such as triethylamine or pyridine. Compounds of formula (II) can be prepared from a compound of formula (XI):

(XI)

in which $R^1$, $R^2$ and P are as defined in formula (I) using standard procedures. For example acid chlorides can be prepared by reaction with phosphorous pentachloride, oxalyl chloride or thionyl chloride. Acid anhydrides can be prepared by reaction with a suitable acid anhydride, for example trifluoroacetic anhydride.

Reaction of a compound of formula (IV) with a nuclephile $R^1$ is preferably carried out in a suitable solvent such as dimethylformamide in the presence of a strong base such as sodium hydride. Preferably the leaving group X is halo, in particular fluoro. Preferably the group $R^2$ is an electron withdrawing group, for example nitro, $COCH_3$ or cyano, in the ortho or para-positions relative to the group X.

Reaction of a compound of formula (V) with a compound of formula (VI) is suitably carried out in an alcohol or nitrile solvent with an optional base or, alternatively, in a non-polar solvent such as chlorobenzene in the absence of base. Suitably, the reactions are carried out at ambient or elevated temperature, preferably at the reflux temperature of the reaction mixture.

Reaction of compounds of formula (VII) and (VIII) and reaction of compounds of formulae (IX) and (X) can be carried out in the presence of a transition metal catalyst such as $Pd(PPh_3)_4$ in a solvent such as an ether in the presence of a base such as an alkali metal carbonate or bicarbonate, for example sodium carbonate or bicarbonate, at ambient or elevated temperature.

Certain compounds of formula (I) can be converted into further compounds of formula (I) using standard procedures. For example $R^2/R^3$ halogens can be introduced by halogenation.

Intermediate compounds of formulae (III), (IV), (V), (VI), (VII), (VIII), (IX), (X) and (XI) are commercially available or can be prepared using standard procedures such as those outlined in EPA 533266/7/8.

Certain compounds of formulae (IV), (V), (VII) and (IX) are novel and form a further aspect of the invention.

It will be appreciated to those skilled in the art that it may be necessary to protect certain reactive substituents during some of the above procedures, for example when the group $R^4$ is a hydrogen atom. Standard protection and deprotection techniques can be used. For example, primary amines can be protected as phthalimide, benzyl, benzyloxycarbonyl or tityl derivatives. These groups can be removed by conventional procedures.

Carboxylic acid groups can be protected as esters. Aldehyde or ketone groups can be protected as acetals, ketals, thioacetals or thioketals. Deprotection is achieved using standard conditions.

$5HT_{1D}$ Antagonists, and in particular the compounds of the present invention, are expected to be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder, memory disorders, including dementia, amnestic disorders and age-associated memory impairment; and disorders of eating behaviours, including anorexia nervosa and bulimia nervosa. Other CNS disorders include Parkinson's disease, dementia in Parkinson's disease, neuroleptic-induced Parkinsonism and tardive dyskinesias, as well as other psychiatric disorders.

$5HT_{1D}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointenstinal tract where changes in motility and secretion are involved. They may also be of use in the treatment of sexual dysfunction.

Therefore, the present invention, provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provdes the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

When administered in accordance with the invention, no unacceptable toxicological effects are expected with the compounds of the invention.

The following Examples illustrate the preparation of pharmacologically active compounds of the invention.

DESCRIPTION 1

2-Bromo-5-pyridinecarboxylic acid 2,5-dibromopyridine (1.0 g;4.22 mmol) was cooled to −78° C. in dry $Et_2O$ (10 ml) under Ar and treated with "BuLi (2.64 ml;4.22 mmol of a 1.6M solution in hexanes) rapidly, stirred for 5 minutes and treated with solid $CO_2$. Allowed to warm to RT, treated with $H_2O$ (10 ml) and the aqueous layer separated then washed with $Et_2O$. The aqueous phase was acidified with conc.HCl(aq) and the precipitate that formed was collected by filtration and dried in vacuo to yield the title compound as a pale yellow solid (0.35 g;41%).
$^1$NMR (250 MHz, $CDCl_3$) δ:8.90(d,1H), 8.20(d,1H), 7.65 (d,1H)

DESCRIPTION 2

5-Bromo-2-thiophenecarboxylic acid

5-Bromo-2-thiophenecarboxaldehyde (1.0 g;5.24 mmol) was dissolved in acetone (4 ml) and treated with 20% $Na_2CO_3$(aq) (0.53 ml). $KMnO_4$ (0.827;5.24 mmol) was added portionwise and the solution stirred for 1 hour at RT. The reaction mixture was filtered through kieselguhr and the filtrate treated with $H_2O_2$ (0.8 ml of a 27% solution in water). When all effervesence had ceased, the aqueous was acidified with conc.HCl(aq) and a yellow solid precipitated. The suspension was extracted with EtOAc, the extracts combined and dried over $Na_2SO_4$, filtered, and the filtrate evaporated in vacuo to a yellow liquid. The liquid was diluted with hexane and cooled to −78° C. The solid that formed was collected by filtration and dried to yield the title compound as a pale yellow solid (0.3 g;28%).
$^1$H NMR (250 MHz, $CDCl_3$) δ:7.65(d,1H), 7.15(d,1H)

DESCRIPTION 3

5-Bromo-N-[4-methoxy-3-(4-methyl-1-piperazinyl) phenyl]furan-2-carboxamide

5-Bromofuroic acid (0.432;2.26 mmol) was heated at reflux in thionyl chloride (10 ml) for 30 minutes, cooled, evaporated in vacuo and the residue azeotroped with toluene. The residue was redissolved in $CH_2Cl_2$ (10 ml) and treated with dry triethylamine (0.32 ml;2.26 mmol) and 4-methoxy-3-(4-methyl-1-piperazinyl)benzenamine (0.5 g;2.26 mmol). The solution was stirred under Ar (18 hours), evaporated in vacuo and partitioned satd. $K_2CO_3$(aq)/ EtOAc. The organic phases were combined, dried over $Na_2SO_4$, filtered and the filtrate evaporated in vacuo to a brown gum. The gum was purified by flash silica-gel chromatography and eluted with 2%MeOH/$CHCl_3$ to yield the title compound as a pale yellow foam (0.77 g;86%), which was converted to the oxalate salt, mp=125°–127° C.
$^1$H NMR (250 MHz, $CDCl_3$) (free base) δ: 7.90(s, 1H), 7.40–7.15(m,3H), 6.85(d,1H), 6.50(d,1H), 3.90(s,3H), 3.25–3.05(m,4H), 2.70–2.50(m,4H), 2.40(s,3H)

DESCRIPTION 4

5-Bromo-N-[4-methoxy-3-(4-methyl-1-piperazinyl) phenyl]furan-3-carboxamide

5-Bromo-3-furancarboxylic acid (0.302;1.58 mmol) was heated at reflux in thionyl chloride (8 ml) for 30 minutes, cooled, evaporated in vacuo and the residue azeotroped with toluene. The residue was redissolved in $CH_2Cl_2$ (10 ml) and treated with dry triethylamine (0.22 ml; 1.58 mmol) and 4-methoxy-3-(4-methyl-1-piperazinyl)benzenamine (0.35 g;1.58 mmol). The solution was stirred under Ar (18 hours), evaporated in vacuo and partitioned satd. $K_2CO_3$(aq)/ EtOAc. The organic phases were combined, dried over $Na_2SO_4$, filtered and the filtrate evaporated in vacuo to a brown gum. The gum was purified by flash silica-gel chromatography and eluted with 3%MeOH/$CHCl_3$ to yield the title compound as a tan solid after trituration with $Et_2O$ (0.3 g;48%), mp=185°–187° C.
$^1$H NMR (250 MHz, $CDCl_3$) (free base) δ:8.85(s,1H), 8.20(s,1H), 7.40(d,1H), 7.15(s,1H), 7.40(s,1H), 6.70(d,1H), 3.80(s,3H), 3.20–2.90(m,4H), 2.80–2.60(m,4H), 2.40(s,3H)

DESCRIPTION 5

5-Bromo-N-[4-methoxy-3-(4-methyl-1-piperazinyl) phenyl]thiophene-2-carboxamide 5-Bromo-2-thiophenecarboxylic acid (0.375;1.8 mmol) was heated at reflux in thionyl chloride (8 ml) for 30 minutes, cooled, evaporated in vacuo and the residue azeotroped with toluene. The residue was redissolved in $CH_2Cl_2$ (10 ml) and treated with dry triethylamine (0.25 ml;1.81 mmol) and 4-methoxy-3-(4-methyl-1-piperazinyl) benzenamine (0.4 g;1.81 mmol). The solution was stirred under Ar (18 hours), evaporated in vacuo and partitioned satd. $K_2CO_3$(aq)/EtOAc. The organic phases were combined, dried over $Na_2SO_4$, filtered and the filtrate evaporated in vacuo to a brown gum. The gum was purified by flash silica-gel chromatography and eluted with 3%MeOH/ $CHCl_3$ to yield the title compound as a brown gum which crystallised on standing (0.388 g;52%), and was converted to the oxalate salt, mp=114°–115° C.
$^1$H NMR (250 MHz, $CDCl_3$) (free base) δ:8.60(s,1H), 7.70(d,1H), 7.50(d,1H), 7.20(s,1H), 7.10(d,1H), 6.80(d,1H), 3.80(s,3H), 3.30–2.75(m,8H), 2.55(s,3H)

DESCRIPTION 6

2-Bromo-N-[4-methoxy-3-(4-methyl-1-piperazinyl) phenyl]pyridine-5-carboxamide 2-Bromo-5-pyridinecarboxylic acid (0.34 g; 1.68 mmol) was heated at reflux in thionyl chloride (8 ml) for 1 hour, cooled, evaporated in vacuo and the residue azeotroped with toluene. The orange residue was redissolved in $CH_2Cl_2$ (6 ml) and treated with dry triethylamine (0.24 ml;1.68 mmol) and 4-methoxy-3-(4-methyl-1-piperazinyl)benzenamine (0.372 g;1.68 mmol). The solution was stirred under Ar (18 hours), evaporated in vacuo and partitioned satd. $K_2CO_3$ (aq)/EtOAc. The organic phases were combined, dried over $Na_2SO_4$, filtered and the filtrate evaporated in vacuo to a brown gum. The gum was purified by flash silica-gel chromatography and eluted with 3%MeOH/$CHCl_3$ to yield the title compound as brown crystals after trituration with acetone/$Et_2O$ (0.13 g;19%).
$^1$H NMR (200 MHz, $CDCl_3$) δ: 9.90(s,1H), 9.00(d,1H), 8.30(d,1H), 7.50–7.30(m,3H), 6.80(d,1H), 3.85(s,3H), 3.30–3.00(m,4H), 2.80–2.65(m,4H), 2.40(s,3H)

DESCRIPTION 7

2-Bromo-N-[4-methoxy-3-(4-methyl-1-piperazinyl) phenyl]-3-methoxythiophene-4-carboxamide 2-Bromo-3-methoxythiophene-4-carboxylic acid (0.429 g; 1.81 mmol) was heated at reflux in thionyl chloride (8 ml) for 1 hour, cooled, evaporated in vacuo and the residue azeotroped with toluene. The orange residue was redissolved in $CH_2Cl_2$ (5 ml) and treated with dry triethylamine (0.25 ml;1.81 mmol) and 4-methoxy-3-(4-methyl-1-piperazinyl)benzenamine (0.4 g; 1.8mmol). The solution was stirred under Ar (18 hours), evaporated in vacuo and partitioned satd. $K_2CO_3$(aq)/EtOAc. The organic phases were combined, dried over $Na_2SO_4$, filtered and the filtrate evaporated in vacuo to a brown gum. The gum was purified by flash silica-gel chromatography and eluted with 2%MeOH/CHCl$_3$ to yield the title compound as white powder after trituration with Et$_2$O (0.43 g;54%), mp=120–122° C.
$^1$H NMR (250 MHz, CDCl$_3$) δ: 9.10(s,1H), 8.10(s,1H), 7.30(d,1H), 7.20(d,1H), 6.80(d,1H), 4.10(s,3H), 3.90(s,3H), 3.25–3.10(m,4H), 2.75–2.60(m,4H), 2.40(s,3H)

DESCRIPTION 8

Ethyl 4-(1,2,4-triazol-1-yl)benzoate 1,2,4-Triazole (0.82 g, 0.01 mol), ethyl 4-fluorobenzoate (2 g, 0.01 mol) and anhydrous potassium carbonate (1.43 g, 0.01 mol) was dissolved in DMSO (30 ml) and heated to 90° C. for 18 h. The solution was poured into water (50 ml), extracted with ethyl acetate (50 ml), dried (sodium sulphate), filtered and evaporated to dryness under reduced pressure. The white solid was purified by flash column chromatography (silica, diethyl ether) to afford a white solid (1.59 g, 73%).
1H NMR (CDCl$_3$) δ1.43 (3H, t), 4.42 (2H, q), 7.81 (2H, d), 8.15 (1H, s), 8.21 (2H, d), 8.68 (1H, s).

DESCRIPTION 9

Ethyl 4-(imidazol-1-yl)benzoate

Imidazole (0.816 g, 0.01 mol), ethyl 4-fluorobenzoate (2 g, 0.01 mol) and anhydrous potassium carbonate (1.43 g, 0.011 mol) was dissolved in DMSO (30 ml) and heated to 90° C. for 18 h. The solution was poured into water (50 ml), extracted with ethyl acetate (50 ml), dried (sodium sulphate), filtered and evaporated to dryness under reduced pressure. The white solid was purified by flash column chromatography (silica, diethyl ether) to afford a white solid (1.22 g, 56%).
1H NMR (CDCl$_3$) δ: 1.43 (3H, t), 4.42 (2H, q), 7.28 (1H, s), 7.38 (1H, s), 7.48 (2H, d), 7.95 (1H, s), 8.19 (2H, d).

DESCRIPTION 10

Ethyl 4-(morpholin-1-yl)benzoate

Morpholine (1.04 ml, 0.011 mol), ethyl 4-fluorobenzoate (2 g, 0.01 mol) and anhydrous potassium carbonate (1.43 g, 0.011 mol) was dissolved in DMSO (30 ml) and heated to 90° C. for 18 h. The solution was poured into water (50 ml), extracted with ethyl acetate (50 ml), dried (sodium sulphate), filtered and evaporated to dryness under reduced pressure. The white solid was purified by flash column chromatography (silica, diethyl ether) to afford a white solid (1.39 g, 59%).
1H NMR (CDCl$_3$) δ: 1.43 (3H, t), 3.24 (4H, q), 3.72 (4H, q), 4.42 (2H, q), 7.00 (2H, d), 7.78 (2H, d).

DESCRIPTION 11

Ethyl 4-(4-ethoxycarbonylpiperazin-1-yl)benzoate

Ethyl 4-fluorobenzoate (0.93 ml, 6.3 mmol), anhydrous potassium carbonate (0.96 g, 7.0 mmol), ethoxycarbonyl piperazine (0.92 ml, 6.3 mmol) and dry DMSO (30 ml) were heated under dry conditions at 90° C. for 72h. The mixture was partitioned between ethyl acetate and water, dried (sodium sulphate) and evaporated to dryness under reduced pressure. The product was purified by flash column chromatography on silica eluting with 10%MeOH/chloroform to afford the title compound as an oil (1.35 g, 70%).

1H NMR (CDCl$_3$) 1.29 (3H, t), 1.38 (3H, t), 3.32 (4H, m), 3.64 (4H, m), 4.19 (2H, q), 4.33 (2H, q), 6.87 (2H, d), 7.95 (2H, d).

EXAMPLE 1

N-(4-Methoxy-3-(4-methyl-1-piperazinyl)phenyl)-4-(1,2,4-triazol-1-yl) benzamide

Ethyl 4-(1,2,4-triazol-1-yl)benzoate (520 mg, 2.4 mmol) was heated at reflux in 5N HCl (40 ml) for 1 h, and the product filtered off and dried in vacuo to afford the acid (88%). 4-(1,2,4triazol-1-yl)benzoic acid (0.395 g, 2.1 mmol) was suspended in dry toluene (40 ml) and thionyl chloride (2 ml) added under argon. The mixture was heated to reflux for 1.5 h and then evaporated to dryness under reduced pressure. The oil was dissolved in dichloromethane under argon and 4-methoxy-3-(4-methyl-1-piperazinyl) phenylamine (460 mg, 2.1 mmol) was added followed by triethylamine (2 ml). The mixture was stirred at room temperature under argon for 2 h and then partitioned between dichloromethane (50 ml) and saturated potassium carbonate (50 ml), and the organic extracts dried (sodium sulphate). The organic solution was filtered, evaporated to dryness under reduced pressure and purified by column chromatography (silica, chloroform/methanol 5–10%) to afford the amide (757 mg, 92%) which was crystallised from methanol diethyl ether as the oxalate salt.
1H NMR (CDCl$_3$) (free base) δ: 2.38 (3H, s ), 2.65 (4H, bm), 3.13 (4H, bm), 3.89 (3H, s), 6.88 (1H, d), 7.22 (1H, s), 7.74 (1H, s), 7.84 (2H, d), 8.03 (2H, d), 8.18 (1H, s), 8.68 (1H, s).

EXAMPLE 2

N-(4-Methoxy-3-(4-methyl-1-piperazinyl)phenyl)-4-(imidazol-1-yl) benzamide

Ethyl 4-(imidazol-1-yl)benzoate (0.5 g, 2.3 mmol) was heated at reflux in 5N HCl (40 ml) for 1 h, evaporated to dryness under reduced pressure and the resulting white solid dried in vacuo to afford 4-(imidazol-1-yl)benzoic acid This was suspended in dry toluene (40 ml) and thionyl chloride (2 ml) added under argon. The mixture was heated to reflux for 1.5 h and then evaporated to dryness under reduced pressure. The oil was dissolved in dichloromethane under argon and 4-methoxy-3-(4-methyl-1-piperazinyl) phenylamine (551 mg, 2.3 mmol) was added followed by triethylamine (2 ml). The mixture was stirred at room temperature under argon for 2 h and then partitioned between dichloromethane (50 ml) and saturated potassium carbonate (50 ml), and the organic extracts dried (sodium sulphate). The organic solution was filtered, evaporated to dryness under reduced pressure and purified by column chromatography (silica, chloroform/methanol 5–10%) to afford the amide (809 mg, 90%) which was crystallised from methanol diethyl ether as the oxalate salt.
1H NMR (CDCl$_3$) (free base) δ: 2.38 (3H, s), 2.66 (4H, bm), 3.15 (4H, bm), 3.90 (3H, s), 6.87 (1H, d), 7.29 (2H, m), 7.37 (1H, s), 7.52 (2H, d), 7.86 (1H, s), 7.93 1H, s), 8.01 (2H, d).

EXAMPLE 3

N-(4-Methoxy-3-(4-methyl-1-piperazinyl)phenyl)-4-(morpholin-1-yl) benzamide

Ethyl 4-(morpholin-1-yl)benzoate (564 mg, 2.4 mmol) was heated at reflux in 5N HCl (40 ml) for 1 h, evaporated to dryness and dried in vacuo to afford 4(morpholin-1-yl)

benzoic acid. This was suspended in dry toluene (40 ml) and thionyl chloride (2 ml) added under argon. The mixture was heated to reflux for 1.5 h and then evaporated to dryness under reduced pressure. The oil was dissolved in dichloromethane under argon and 4-methoxy-3-(4-methyl-1-piperazinyl)phenylamine (530 mg, 2.4 mmol) was added followed by triethylamine (2 ml). The mixture was stirred at room temperature under argon for 2 h and then partitioned between dichloromethane (50 ml) and saturated potassium carbonate (50 ml), and the organic extracts dried (sodium sulphate). The organic solution was filtered, evaporated to dryness under reduced pressure and purified by column chromatography (silica, chloroform/methanol 5–10%) to afford the amide (925 mg, 94%) which was crystallised from methanol diethyl ether as the oxalate salt.

1H NMR (CDCl$_3$) (free base) δ: 2.35 (3H, s ), 2.62 (4H, bm), 3.14 (4H, bm), 3.28 (4H, m), 3.89 (7H, s and m), 6.83 (1H, d), 6.93 (2H, d), 7.22 (1H, s), 7.62 (1H, s), 7.80 (2H, d).

EXAMPLE 4

N-(4-Methoxy-3-(4-methyl-1-piperazinyl)phenyl)-4-(3-thiophenyl)-3-methylbenzamide N-(4Methoxy-3-(4-methyl-1-piperazinyl)phenyl)-4-bromo-3-methylbenzamide (0.35 g, 0.84 mmol), sodium carbonate (89 mg, 0.84 mmol), tetrakis (triphenylphosphine)palladium(0) (49 mg, 0.05 equiv), 3-thiophenyl boronic acid (115 mg, 0.84 mmol) in water (18 ml) and DME (18 ml) were heated at reflux under argon for 18 h. The solution was partitioned between saturated aqueous potassium carbonate solution (50 ml) and chloroform (50 ml), the organic extracts dried (sodium sulphate), filtered and evaporated to dryness under reduced pressure. The resulting oil was purified by column chromatography (silica, chloroform/methanol 5–30%) to afford the tide compound as an oil (242 mg, 63%) which was crystallised as an oxalate salt from methanol chloroform.

1H NMR (D6-DMSO) δ: 2.42 (3H, s), 2.82 (3H, s), 3.32 (8H, bm, 4xCH$_2$), 3.80 (3H, s), 6.98 (1H d), 7.32 (1H, d), 7.46 (3H, m), 7.68 (2H, m), 7.81 (1H, d), 7.90 (1H, d).
Mass Spectrum M$^+$ found 421, C$_{24}$H$_{27}$N$_3$O$_2$S requires 421
Analysis Found C 53.26; H 5.03; N 6.63. C$_{24}$H$_{27}$N$_3$O$_2$S.2C$_2$H$_2$O$_4$.1.5H$_2$O requires C 53.50; H 5.41; N 6.69.

EXAMPLE 5

N-(4-Methoxy-3-(4-methyl-1-piperazinyl)phenyl)-4-(1,2,4-triazol-1-yl)-3-nitrobenzamide oxalate 4-(1,2,4-triazol-1-yl)-3-nitrobenzoic acid (100 mg, 0.43 mmol) was suspended in dry toluene (40 ml) and thionyl chloride (1 ml) added under argon. The mixture was heated at reflux for 1.5 h and the resulting yellow solution evaporated to dryness under reduced pressure. The oil was dissolved in dry dichloromethane (40 ml) under argon and 4methoxy-5-(4-methyl-1-piperazinyl)phenylamine (94mg, 0.43 mmol) was added followed by triethylamine (0.06 ml). The mixture was stirred for 2 h under argon, partitioned between dichloromethane and saturated aqueous potassium carbonate(50 ml) and the organic extracts dried (sodium sulphate). The solution was evaporated to dryness under reduced pressure and purified by column chromatography (silica, chloroform/methanol 5–10%) to afford the amide (153 mg,81%) as an oil which was crystallised from methanol/diethyl ether as the oxalate salt, m.p. 223°–225° C.
1H NMR (CDCl$_3$) (free base) δ2.68 (4H, bm), 3.10 (4H, bm), 3.51 (3H, s), 3.89 (3H, s), 6.83 (1H, d), 7.18 (1H, s), 7.38 (1H, dd), 7.69 (1H, d), 8.15 (1H, d), 8.31 (1H, dd), 8.53 (2H, d), 8.90 (1H, bs, NH).
Mass Spectrum M+437. C$_{21}$H$_{23}$N$_7$O$_4$ requires 437
Analysis C 52.44, H 5.11, N 18.87 C$_{21}$H$_{23}$N$_7$O$_4$.C$_2$H$_2$O$_4$ requires C 52.37, H 4.78, N 18.59.

EXAMPLE 6

N-[4-methoxy-3-(4-methyl-1-piperazinyl)phenyl]-5-(4-pyridyl)furan-2-carboxamide 5-bromo-N-[4-methoxy-3-(4-methyl-1-piperazinyl) phenyl]furan-2-carboxamide (0.3 g;0.76 mmol) was stirred with 4-pyridylboronic acid (0.094 g;0.76 mmol), tetrakis (triphenylphosphine)palladium(0) (0.045 g;5 mol %) and anhydrous sodium carbonate (0.089 g;0.84 mmol) in water (14 ml) and DME (14 ml) and the whole heated at reflux under Ar (18 hours). The reaction mixture was poured into 10% Na$_2$CO$_3$(aq) (30 ml) and extracted into CHCl$_3$. The organic extracts were combined, dried over Na$_2$SO$_4$, filtered and the filtrate evaporated in vacuo to a brown oil which crystallised on standing. The brown solid was purified by flash silica-gel chromatography and eluted with 3%MeOH/CHCl$_3$ to yield the title compound as a lemon solid (0.22 g;74%), mp=157°–159° C.
$^1$H NMR (200 MHz, CDCl$_3$) δ: 8.70(d,2H), 8.00(s,1H), 7.60(d,2H), 7.35–7.15(m,3H), 7.00(d,1H), 6.85(d,1H) 3.85 (s,3H), 3.20–3.05(m,4H), 2.70–2.55(m,4H), 2.35(s,3H)

EXAMPLE 7

N-[4-methoxy-3-(4-methyl-1-piperazinyl)phenyl]-5-(4-pyridyl)furan-3-carboxamide 5-bromo-N-[4-methoxy-3-(4-methyl- 1-piperazinyl) phenyl]furan-3-carboxamide (0.16 g;0.41 mmol) was stirred with 4-pyridylboronic acid (0.050 g;0.41 mmol), tetrakis (triphenylphosphine)palladium(0) (0.024 g;5 mol %) and anhydrous sodium carbonate (0.047 g;0.45 mmol) in water (8 ml) and DME (8 ml) and the whole heated at reflux under Ar (18 hours). The reaction mixture was poured into 10% Na$_2$CO$_3$(aq) (20 ml ) and extracted into CHCl$_3$. The organic extracts were combined, dried over Na$_2$SO$_4$, filtered and the filtrate evaporated in vacuo to a brown gum. The gum was purified by flash silica-gel chromatography and eluted with 4%MeOH/CHCl$_3$ to yield a orange oil which was triturated with hexane/Et$_2$O. The solid that formed was collected by filtration and dried in vacuo to yield the title compound as a tan solid (0.029 g;18%), mp=103°–105° C.
$^1$H NMR (250 MHz, CDCl$_3$) δ: 8.65(d,2H), 8.15(s,1H), 7.65(s,1H), 7.55(d,2H), 7.35–7.10(m,3H), 6.85(d,1H) 3.90 (s,3H), 3.20(m,4H), 2.70–2.55(m,4H), 2.40(s,3H)

EXAMPLE 8

N-[4-methoxy-3-(4-methyl-1-piperazinyl)phenyl]-5-(4-pyridyl)thiophene-2-carboxamide 5-bromo-N-[4-methoxy-3-(4-methyl-1-piperazinyl) phenyl]thiophene-2-carboxamide (0.31 g;0.76 mmol) was stirred with 4-pyridylboronic acid (0.093 g;0.76 mmol), tetrakis(triphenylphosphine)palladium(0) (0.045 g;5 mol %) and anhydrous sodium carbonate (0.089 g;0.84 mmol) in water (14 ml) and DME (14 ml) and the whole heated at reflux under Ar (18 hours). The reaction mixture was poured into 10% Na$_2$CO$_3$(aq) (30 ml) and extracted into CHCl$_3$. The organic extracts were combined, dried over Na$_2$SO$_4$, filtered and the filtrate evaporated in vacuo to a brown gum. The gum was purified by flash silica-gel chromatography and eluted with 4%MeOH/CHCl₃ to yield a yellow, semi-solid residue which was triturated with acetone/Et₂O. The solid that formed was collected by filtration and dried in vacuo to yield the tide compound as a yellow solid (0.2 g;65%), mp=191–194° C.
¹H NMR (250 MHz, CDCl₃) δ: 8.65(d,2H), 7.90(s,1H), 7.60(d,1H), 7.55–7.45(m,3H), 7.30–7.20(m,2H), 6.80(d, 1H), 3.90(s,3H), 3.25–3.05(m,4H), 2.70–2.55(m,4H), 2.40 (s,3H)

EXAMPLE 9

N-[4-methoxy-3-(4-methyl-1-piperazinyl)phenyl]-2-(4-pyridyl)pyridine-5-carboxamide 2-Bromo-N-[4-methoxy-3-(4-methyl-1-piperazinyl) phenyl]pyridine-5-carboxamide (0.125 g;0.31 mmol) was stirred with 4-pyridylboronic acid (0.038 g;0.31 mmol), tetrakis(triphenylphosphine)palladium(0) (0.024 g) and anhydrous sodium carbonate (0.036 g;0.34 mmol) in water (5 ml) and DME (5 ml) and the whole heated at reflux under Ar (18 hours). The reaction mixture was poured into 10% Na₂CO₃(aq) (20 ml) and extracted into CHCl₃. The organic extracts were combined, dried over Na₂SO₄, filtered and the filtrate evaporated in vacuo to a brown gum. The gum was purified by flash silica-gel chromatography and eluted with 5%MeOH/CHCl₃ to yield a orange/yellow gum(0.060 g;48%).
¹H NMR (200 MHz, CDCl₃) δ: 9.20(s,1H), 8.75(s,2H), 8.60(s,1H), 8.35(d,1H), 8.00–7.85(m,3H), 7.40(d,1H), 7.25 (d,1H), 6.85(d,1H), 3.85(s,3H), 3.20–3.05(m,4H), 2.75–2.60(m,4H), 2.40(s,3H)

EXAMPLE 10

N-[4-methoxy-3-(4-methyl-1-piperazinyl)phenyl]-2-(4-pyridyl)-3-methoxythiophene-4-carboxamide 2-Bromo-N-[4-methoxy-3-(4-methyl- 1-piperazinyl) phenyl]-3-methoxythiophene-4-carboxamide (0.20 g;0.45 mmol) was stirred with 4-pyridylboronic acid (0.056 g;0.45 mmol), tetrakis(triphenylphosphine)palladium(0) (0.024 g) and anhydrous sodium carbonate (0.053 g;0.50 mmol) in water (5 ml) and DME (5 ml) and the whole heated at reflux under Ar (18 hours). The reaction mixture was poured into 10% Na₂CO₃(aq) (20 ml) and extracted into CHCl₃. The organic extracts were combined, dried over Na₂SO₄, filtered and the filtrate evaporated in vacuo to a brown gum. The gum was purified by flash silica-gel chromatography and eluted with 4%MeOH/CHCl₃ to yield a orange gum (0.088;44%).
¹H NMR (200 MHz, CDCl₃) δ: 9.20(s,1H), 8.70(d,2H), 8.20(s,1H), 7.60(d,2H), 7.35–7.20(m,2H), 6.85(d,1H), 3.90 (s,3H), 3.85(s,3H), 3.25–3.10(m,4H), 2.75–2.60(m,4H), 2.40(s,3H)

EXAMPLE 11

N-[4-methoxy-3-(4-methyl-1-piperazinyl)phenyl]-5-(2-pyridyl)thiophene-2-carboxamide 5-(pyrid-2-yl)thiophene-2-carboxylic acid (0.279 g; 1.36 mmol) was heated at reflux in thionyl chloride (8 ml) for 1 hour, cooled, evaporated in vacuo and the residue azeotroped with toluene. The orange residue was redissolved in CH₂Cl₂ (10 ml) and treated with dry triethylamine (0.19 ml; 1.36 mmol) and 4-methoxy-3-(4-methyl-1-piperazinyl) benzenamine (0.3 g;1.36 mmol). The solution was stirred under Ar (18 hours), evaporated in vacuo and partitioned satd. K₂CO₃(aq)/EtOAc. The organic phases were combined, dried over Na₂SO₄, filtered and the filtrate evaporated in vacuo to a brown gum. The gum was purified by flash silica-gel chromatography and eluted with 2%MeOH/CHCl₃ to yield the title compound as a orange gum (0.37 g;67%), which was converted to the oxalate salt, mp=131° C.(dec).
¹H NMR (250 MHz, CDCl₃) (free base) δ: 8.55(d,1H), 8.45(s,1H), 7.80–7.60(m,3H), 7.55(d,1H), 7.40–7.30(m, 1H), 7.25–7.15(m,2H), 6.80(d,1H), 3.85(s,3H), 3.20–3.00 (m,4H), 2.70–2.50(m,4H), 2.35(s,3H)

EXAMPLE 12

N-(4-Methoxy-3-(4-methyl-1-piperazinyl)phenyl)-3-nitro-4-pyrazolylbenzamide

As for Example 5 using 3-nitro-4-pyrazolylbenzoic acid (200 mg, 0.86 mmol), toluene (40 ml), thionyl chloride (2 ml), and DCM (40 ml), triethylamine (2 ml) and the amine (189 mg, 0.85 mmol). The resulting oil was purified by column chromatography (silica, chloroform/methanol 5–30%) to afford the title compound as an oil (371 mg, 100%) which was crystallised as an oxalate salt from methanol/chloroform.
1H NMR (D6DMSO) 2.78 (3H, s), 3.73 (8H, bm, 4xCH₂), 3.81 (3H, s), 6.65 (1H m), 7.01 (1H, d), 7.41 (1H, m), 7.50 (1H, d), 7.82 (1H, m), 8.00 (1H, d), 8.37 (1H, m), 8A6 (1H, m), 8.53 (1H, m), 10.41 (1H, bs, NH)
Mass Spectrum M⁺ found 436 C₂₂H₂₄N₆O₄ requires 436
Analysis Found C 54.32; H 4.92; N 15.73. C₂₂H₂₄N₆O₄.1.1C₂H₂O₄ requires C 54.28; H 4.90; N 15.70.

EXAMPLE 13

N-(4-Methoxy-3-(4-methyl-1-piperazinyl)phenyl)-4-(4-ethoxycarbonylpiperazin-1-yl)benzamide Ethyl 4-(4-ethoxycarbonylpiperazin-1-yl)benzoate (0.5 g, 1.6 mmol), conc.HCl (10 ml) and 5N HCl (20 ml) were heated at reflux for 45 min, evaporated to dryness and dried in vacuo. The white solid was suspended in thionyl chloride (2 ml) and dry toluene (40 ml) and heated at reflux for 1 h. The brown solution was evaporated to dryness under reduced pressure and dissolved in DCM (40 ml), triethylamine (3 ml) and N-4-methoxy-3-(4-methyl-1-piperazinyl) phenylamine(360 mg,1.6 mmol) added. The solution was stirred for 30 min, partitioned between chloroform and saturated aqueous potassium carbonate solution, the organic solutions dried (sodium sulphate) and evaporated to dryness under reduced pressure. The solid was purified by flash column chromatography using silica and eluting with chloroform/MeOH (4–10%) to afford the tide compound as a solid (295 mg, 38%).
1H NMR (CDCl₃) 1.31 (3H, t), 2.41 (3H, s), 2.63 (4H, bs), 3.15 (4H, bs), 3.31 (4H, bm), 3.66 (4H, bm), 3.88 (3H, s), 4.19 (2H, q), 6.85 (1H, d), 6.95 (2H, d), 7.30 (1H, s), 7.65 (1H, s), 7.80 (2H, d).
Mass Spectrum M⁺ found 481 C₂₆H₃₅N₅O₄ requires 481

EXAMPLE 14

N-(4-Methoxy-3-(4-methyl-1-piperazinyl)phenyl)-4-fluorobenzamide

4-Fluorobenzoyl chloride (0.23 ml, 1.95 mmol) with 4-methoxy-3-(4-methyl-1-piperazinyl)phenylamine (400 mg, 1.95 mmol) in dry dichloromethane (40 ml) and triethylamine (1 ml) was stirred for 1 h. The solution was partitioned between dichloromethane (40 ml) and saturated aqueous potassium carbonate (40 ml), the organic solution dried (sodium sulphate) and evaporated to dryness under reduced pressure to afford an oil, which was purified by column chromatography (silica, chloroform,/methanol 5%) to afford the tide compound (595 mg, 89%) which was crystallised from methanol/diethyl ether as the oxalate salt.
1H nmr (d6-DMSO) δ 2.77 (3H, s), 3.25 (8H, bs), 3.81 (3H, s), 6.99 1H, d), 7.38 (3H, m), 7.48 (1H, d), 8.04 (2H, d), 10.12 (1H, s, NH).
Mass spectrum M$^+$ 343 $C_{19}H_{22}N_3O_2$ requires 343.
Elemental analysis C 56.72, H 5.58, N 9.25% $C_{19}H_{22}N_3O_2 \cdot 1.2(C_2H_2O_4)$ requires C 56.94, H 5.41, N 9.31%

EXAMPLE 15

N-(4-Methoxy-3-(4-methyl-1-piperazinyl)phenyl)-4-chlorobenzamide

4-Chlorobenzoic acid (350 mg, 2.23 mmol) was heated at reflux with thionyl chloride (3 ml) and toluene (40 ml) for 2 h, and then evaporated to dryness under reduced pressure. 4-Methoxy-3-(4-methyl-1-piperazinyl)phenylamine (494 mg, 2.23 mmol) in dry dichloromethane (40 ml) was added with triethylamine (2 ml) and the mixture stirred for 1 h. The solution was partitioned between dichloromethane (40 ml) and saturated aqueous potassium carbonate (40 ml), the organic solution dried (sodium sulphate) and evaporated to dryness under reduced pressure to afford an oil, which was purified by column chromatography (silica, chloroform,/methanol 5%) to afford the title compound (774 mg, 97%) which was crystallised from methanol/diethyl ether as the oxalate salt.
1H nmr (free base) (CDCl$_3$) δ 2.38 (3H, s), 2.64 (4H, bs), 3.14 (4H, bs), 3.89 (3H, s), 6.85 (1H, d), 7.20 (1H, s), 7.48 (1H, d), 7.68 (1H, s), 7.81 (1H, d).

EXAMPLE 16

N-(4-Methoxy-3-(4-methyl-1-piperazinyl)phenyl)-4-iodobenzanide

4-Iodobenzoic acid (350 mg, 1.60 mmol) was heated at reflux with thionyl chloride (3 ml) and toluene (40 ml) for 2 h, and then evaporated to dryness under reduced pressure. 4-Methoxy-3-(4-methyl-1-piperazinyl)phenylamine (350 mg, 1.60 mmol) in dry dichloromethane (40 ml) was added with triethylamine (2 ml) and the mixture stirred for 1 h. The solution was partitioned between dichloromethane (40 ml) and saturated aqueous potassium carbonate (40 ml), the organic solution dried (sodium sulphate) and evaporated to dryness under reduced pressure to afford an oil, which was purified by column chromatography (silica, chloroform/methanol 5%) to afford the tide compound (649 mg, 90%) which was crystallised from methanol/diethyl ether as the oxalate salt.
1H nmr (free base) (CDCl$_3$) δ 2.38 (3H, s), 2.68 (4H, bs), 3.19 (4H, bs), 3.89 (3H, s), 6.85 (1H, d), 7.20 (1H, s), 7.60 (1H, d), 7.68 (1H, s), 7.82 (1H, d).

EXAMPLE 17

N-(4-Methoxy-3-(4-methyl-1-piperazinyl)phenyl)-4-cyclohexylbenzamide

4-Cyclohexylbenzoic acid (300 mg, 1.5 mmol) was heated at reflux with thionyl chloride (2 ml) and toluene (40 ml) for 2 h, and then evaporated to dryness under reduced pressure. 4-Methoxy-3-(4-methyl-1-piperazinyl)phenylamine (325 mg, 1.5 mmol) in dry dichloromethane (40 ml) was added with triethylamine (2 ml) and the mixture stirred for 1 h. The solution was partitioned between dichloromethane (40 ml) and saturated aqueous potassium carbonate (40 ml), the organic solution dried (sodium sulphate) and evaporated to dryness under reduced pressure to afford an oil, which was purified by flash column chromatography (silica, chloroform/methanol 5%) to afford the title compound (561 mg, 92%) which was crystallised from methanol/diethyl ether as the oxalate salt m.p. 117°–119° C.
1H nmr (d6-DMSO) δ 1.41 (5H, m), 1.78 (5H, m), 2.58 (1H, m), 2.78 (3H, s, NMe), 3.25 (8H, m), 3.78 (3H, s, OMe), 6.94 (1H, d), 7.34 (2H, d), 7.45 (2H, m), 7.85 (2H, d), 10.00 (1H, s, NH).
Mass spectrum M$^+$ 407 $C_{25}H_{33}N_3O_2$ requires 407.
Elemental analysis C 64.33, H 6.88, N 8.30% $C_{19}H_{22}N_3O_2 \cdot 1.2(C_2H_2O_4)$ requires C 64.03, H 7.11, N 8.30%

EXAMPLE 18

N-(4-Methoxy-3-(4-methyl-1-piperazinyl)phenyl)-4-tert-butylbenzamide

4-'Butylbenzoic acid (300 mg, 1.7 mmol) was heated at reflux with thionyl chloride (2 ml) and toluene (40 ml) for 2 h, and then evaporated to dryness under reduced pressure. 4-Methoxy-3-(4methyl-1-piperazinyl)phenylamine (370 mg, 1.6 mmol) in dry dichloromethane (40 ml) was added with triethylamine (2 ml) and the mixture stirred for 1 h. The solution was partitioned between dichloromethane (40 ml) and saturated aqueous potassium carbonate (40 ml), the organic solution dried (sodium sulphate) and evaporated to dryness under reduced pressure to afford an oil, which was purified by flash column chromatography (silica, chloroform,/methanol 5%) to afford the title compound (720 mg, 100%) which was crystallised from methanol/diethyl ether as the oxalate salt m.p.220°–222° C.
1H nmr (d6-DMSO) δ 1.35 (9H, s), 2.80 (3H, s), 3.23 (8H, bm), 3.80 (3H, s), 6.96 (1H, d), 7.49 (5H, m), 7.89 (2H, d), 10.04 (1H, s, NH).
Mass spectrum M$^+$ 381 $C_{23}H_{31}N_3O_2$ requires 381.
Elemental analysis C 63.15, H 6.89, N 8.91% $C_{23}H_{31}N_3O_2 \cdot 1.1(C_2H_2O_4)$ requires C 63.00, H 6.92, N 8.75%

We claim:

1. A compound of formula (I) or a pharmaceutically acceptable salt thereof:

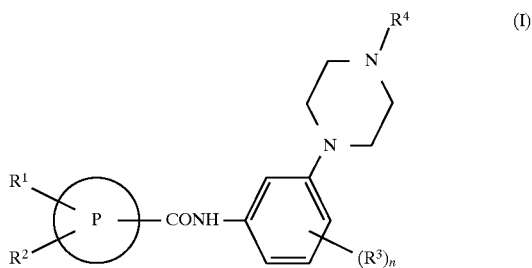

in which

P is thienyl or furyl;

$R^1$ is $C_{1-6}$alkyl, $C_{1-6}$cycloalkyl, phenyl or pyridyl;

$R^2$ is hydrogen, $C_{1-6}$alkoxy;

$R^3$ is halogen, hydroxy, $C_{1-6}$alkyl or $C_{1-6}$alkoxy;

$R^4$ is hydrogen or $C_{1-6}$alkyl; and n is 0, 1 or 2.

2. A compound according to claim 1 in which $R^1$ is butyl, cyclohexyl or pyridyl.

3. A compound according to claim 1 in which $R^3$ is $C_{1-6}$alkoxy.

4. A compound according to claim 1 in which $R^4$ is $C_{1-6}$alkyl.

5. A compound according to claim 1 which is:

N-[4-methoxy-3-(4-methyl-1-piperazinyl)phenyl]-5-(4-pyridyl)furan-2-carboxamide, N-[4-methoxy-3-(4-methyl-1-piperazinyl)phenyl]-5-(4-pyridyl)furan-3-carboxamide, N-[4-methoxy-3-(4-methyl-1-piperazinyl)phenyl]-5-(4-pyridyl)thiophene-2-carboxamide, N-[4-methoxy-3-(4-methyl-1-piperazinyl)phenyl]-2-(4-pyridyl)-3-methoxythiophene-4-carboxamide, or N-[4-methoxy-3-(4-methyl-1-piperazinyl)phenyl]-5-(2-pyridyl)thiophene-2-carboxamide, or pharmaceutically acceptable salts thereof.

6. A process for the preparation of a compound of claim 1 which comprises (a) reaction of a compound of formula (II):

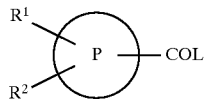

in which $R^1$, $R^2$ and P are as defined in claim 1 and L is a leaving group, with a compound of formula (III):

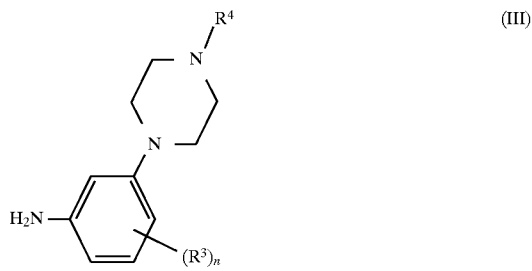

in which $R^3$, $R^4$ and n are as defined in claim 1 and thereafter optionally forming a pharmaceutically acceptable salt.

7. A pharmaceutical composition which comprises a compound according to claim 1 in association with a pharmaceutically acceptable carrier or excipient.

8. A method of treating depression or anxiety which method involves treating a patient in need thereof with a therapeutically effective amount of a compound of claim 1.

* * * * *